(12) United States Patent
Liu et al.

(10) Patent No.: US 12,220,413 B2
(45) Date of Patent: Feb. 11, 2025

(54) MAGNETIC NANO-DRUG WITH DOUBLE TARGETING VEGF-VEGFR, AND PREPARATION METHOD AND APPLICATION THEREOF

(71) Applicant: The Third Clinical Medical College, Nanjing University of Chinese Medicine, Nanjing (CN)

(72) Inventors: Xin Liu, Nanjing (CN); Ran Kang, Nanjing (CN); Lin Xie, Nanjing (CN); Congyang Xue, Nanjing (CN); Bo Chen, Nanjing (CN); Zihan Wang, Nanjing (CN); Nan Wang, Nanjing (CN); Liping Chen, Nanjing (CN)

(73) Assignee: The Third Clinical Medical College, Nanjing University of Chinese Medicine, Nanjing (CN)

(*) Notice: Subject to any disclaimer, the term of this patent is extended or adjusted under 35 U.S.C. 154(b) by 0 days.

(21) Appl. No.: 18/765,361

(22) Filed: Jul. 8, 2024

(65) Prior Publication Data
US 2025/0017920 A1   Jan. 16, 2025

(30) Foreign Application Priority Data
Jul. 11, 2023   (CN) .......................... 202310853646.3

(51) Int. Cl.
| | | |
|---|---|---|
| A61K 31/4965 | (2006.01) | |
| A61K 9/51 | (2006.01) | |
| A61K 38/44 | (2006.01) | |
| A61K 41/00 | (2020.01) | |
| A61K 47/60 | (2017.01) | |
| A61K 47/69 | (2017.01) | |

(52) U.S. Cl.
CPC ........ *A61K 31/4965* (2013.01); *A61K 9/5115* (2013.01); *A61K 9/5169* (2013.01); *A61K 38/443* (2013.01); *A61K 41/0052* (2013.01); *A61K 47/60* (2017.08); *A61K 47/6923* (2017.08); *C12Y 101/01027* (2013.01)

(58) Field of Classification Search
CPC .................................................. A61K 31/4965
See application file for complete search history.

(56) References Cited

FOREIGN PATENT DOCUMENTS

CN        103893128       *   7/2014

\* cited by examiner

*Primary Examiner* — Carlos A Azpuru
(74) *Attorney, Agent, or Firm* — Hemisphere Law, PLLC; Zhigang Ma

(57) ABSTRACT

The present disclosure provides a magnetic nano-drug with double targeting vascular endothelial growth factor (VEGF)-vascular endothelial growth factor receptor (VEGFR), and a preparation method and application thereof, and belongs to the technical field of biomedicine. The magnetic nano-drug of the present disclosure includes aminated $ZnFe_2O_4$ hollow porous magnetic nano-particles, lactate dehydrogenase-silk fibroin (LDH-SF), ethylene dichloride (EDC), and n-hydroxy succinimide (NHS). A mass ratio of the aminated $ZnFe_2O_4$ hollow porous magnetic nano-particles to the EDC to the NHS to the LDH-SF is (5-10):(1-5):(1-6):(1-8).

5 Claims, 5 Drawing Sheets

MAGNETIC NANO-DRUG WITH DOUBLE TARGETING VEGF-VEGFR, AND PREPARATION METHOD AND APPLICATION THEREOF

TECHNICAL FIELD

The present disclosure relates to the technical field of biomedicine, and in particular to a magnetic nano-drug with double targeting vascular endothelial growth factor (VEGF)-vascular endothelial growth factor receptor (VEGFR), and a preparation method and an application thereof.

BACKGROUND

Intervertebral disc degeneration (IDD) is a common disease of orthopedics and traumatology that seriously affects patients' physical and mental health. Its main clinical symptoms include lumbosacral pain, lower-limb radiating pain, and even serious disability. Its pathogenesis involves a series of symptoms, such as protrusion of nucleus pulposus in an intervertebral disc caused by disruption of a fibrous ring, stimulation or/and compression of adjacent spinal nerve root/cauda equina, and discogenic pain and numbness caused by nerve and blood vessels growing into the intervertebral disc. The discogenic pain, one of degenerative symptoms, can lead to the most serious and extensive influence. At present, clinical methods for relieving the pain mainly involve analgesics, surgery, biotherapy, and some traditional Chinese medicine manipulative therapy. Although these methods have some effects in relieving pain, they still cannot completely reverse/eliminate the key cause of pain, that is, vascularization, and also cause serious adverse reactions. For example, long-term use of the analgesics may produce serious side effects and tolerance. Complications may be caused, such as adjacent segment injuries and stenosis after an intervertebral disc fusion operation. The biotherapy has high cost, and the traditional Chinese medicine manipulative therapy cannot relieve severe pain. Therefore, it is one of the important methods for reversing/eliminating pain by taking certain inhibitory strategies against the root cause, which is vascularization, of the discogenic pain. A vascular endothelial growth factor (VEGF) and a vascular endothelial growth factor receptor (VEGFR) play a crucial role in an intervertebral disc vascularization process. However, there is still a lack of bispecific immunotherapy for the VEGF and the VEGFR in clinic.

SUMMARY

In view of this, an objective of the present disclosure is to provide a magnetic nano-drug with double targeting vascular endothelial growth factor (VEGF)-vascular endothelial growth factor receptor (VEGFR), and a preparation method and an application thereof. The magnetic nano-drug according to the present disclosure reaches a disease area through double targeting under the action of a magnetic field, inhibits action of a ligand and a receptor, further inhibits vascularization, blocks neurotrophic supply, and implements radical treatment of pain.

To achieve the above objective, the present disclosure provides the following technical solution:

A magnetic nano-drug with double targeting VEGF-VEGFR includes aminated $ZnFe_2O_4$ hollow porous magnetic nano-particles, ligustrazine hydrochloride nano-spheres lactate dehydrogenase-silk fibroin (LDH-SF), ethylene dichloride (EDC), and n-hydroxy succinimide (NHS). The LDH-SF includes silk fibroin (SF) and ligustrazine hydrochloride (LTH). A mass ratio of the aminated $ZnFe_2O_4$ hollow porous magnetic nano-particles to the EDC to the NHS to the LDH-SF is (5-10):(1-5):(1-6):(1-8).

In some implementations, an amination modification of the aminated $ZnFe_2O_4$ hollow porous magnetic nano-particles is polyethylene glycol (PEG)-$NH_2$.

In some implementations, a mass ratio of the silk fibroin to the ligustrazine hydrochloride is 10:(1-2.5).

In some implementations, the aminated $ZnFe_2O_4$ hollow porous magnetic nano-particles are chemically combined with the LDH-SF nano-spheres through amide bonds activated by EDC/NHS.

In some implementations, a particle size of the aminated $ZnFe_2O_4$ hollow porous magnetic nano-particles is 20 nm-100 nm. A particle size of the LDH-SF is smaller than that of the aminated $ZnFe_2O_4$ hollow porous magnetic nano-particles. The LDH-SF may enter the hollow porous magnetic nano-particles.

The present disclosure further provides a preparation method of the magnetic nano-drug according to one of the above technical solutions. The preparation method includes the following steps:

S1, preparing aminated $ZnFe_2O_4$ hollow porous magnetic nano-particles: dissolving $ZnCl_2$ and $FeCl_3 \cdot 6H_2O$ in an organic solvent, adding NaAc and polyethylene glycol (PEG) 20000, conducting magnetic stirring, adding PEG-$NH_2$ after reaction, conducting stirring again, and conducting cleaning and drying, such that the aminated $ZnFe_2O_4$ hollow porous magnetic nano-particles are obtained;

S2, preparing LDH-SF: mixing a SF solution with a LTH aqueous solution, adding anhydrous ethanol, and conducting secondary stirring, incubation, emulsifying, dialysis, and freeze-drying, such that LTH-SF is obtained; and S3, dissolving the aminated $ZnFe_2O_4$ hollow porous magnetic nano-particles and the LTH-SF separately in a 2-morpholinoethanesulphonic acid (MES) buffer solution, adding EDC/NHS for activation, conducting stirring and mixing for reaction at a room temperature in the dark, and conducting centrifuging and freeze-drying, such that the magnetic nano-drug is obtained.

In some implementations, the organic solvent in the S1 is one or two of ethylene glycol and dimethyl formamide (DMF). Stirring time of magnetic stirring is 30 min-60 min. The reaction is conducted for 8 h-12 h at 150° C.-250° C. Stirring is conducted again for 2 h-4 h at 50° C.-60° C. in a water bath. Cleaning is conducted with ethanol 3 times-6 times. Drying is conducted for 6 h-12 h at 50° C.-70° C. A volume concentration of the ethanol is 75%-100%.

In some implementations, a mmol:mmol:mL:g:g ratio of the $ZnCl_2$ to the $FeCl_3 \cdot 6H_2O$ to the organic solvent to the NaAc to the PEG 20000 in S1 is 2.5:5:(40-50):(3.5-4):(1-1.2), which are sealed in a container after magnetic stirring. After the reaction, the solution needs to be cooled to a room temperature. According to the present disclosure, the hollow porous magnetic nano-particles are prepared through an improved hydrothermal synthesis method, and the $ZnFe_2O_4$ nano-particles having high monodispersity, a uniform particle size and a hollow porous structure are synthesized by controlling conditions such as a raw material ratio, a reagent type, and heat treatment time. Then, the nano-particles are aminated with the PEG-$NH_2$, and finally the aminated $ZnFe_2O_4$ hollow porous magnetic nano-particles are obtained, which are used as targeting ligand VEGF substances.

In some implementations, mixing and stirring in the S2 are conducted for 20 min-30 min at 20° C.-25° C. A volume ratio of the anhydrous ethanol to SF is (2-3):5. Secondary stirring is conducted for 3 min-10 min at 20° C.-25° C. Incubation is conducted for 20 h-24 h at −20° C. to −30° C. Dialysis is conducted in deionized water for 4 h-6 h with a dialysis bag of 12000 Da-14000 Da. According to the present disclosure, the ligustrazine hydrochloride and the silk fibroin are prepared into the nano-spheres through an emulsification method, such that carboxylation modifications of the ligustrazine can be increased, and metabolic stability of the ligustrazine can be enhanced.

In some implementations, a pH value of the MES buffer solution in S3 is 4-6. Stirring and mixing reaction is conducted for 48 h-60 h at 20° C.-25° C. The room temperature is 20° C.-25° C. Centrifuging is conducted at 1000 rpm-2000 rpm for 1 min.

The present disclosure further provides application of the magnetic nano-drug according to any one of the above technical solutions in preparing a drug for anti-angiogenesis and/or discogenic pain treatment.

Beneficial effects are as follows: the present disclosure provides the magnetic nano-drug with double targeting VEGF-VEGFR, and the preparation method and application thereof, and the magnetic nano-drug includes the aminated $ZnFe_2O_4$ hollow porous magnetic nano-particles, the ligustrazine hydrochloride nano-spheres LDH-SF, the EDC, and the NHS; the LDH-SF includes the silk fibroin (SF) and the ligustrazine hydrochloride (LTH); and the mass ratio of the aminated $ZnFe_2O_4$ hollow porous magnetic nano-particles to the EDC to the NHS to the LDH-SF is (5-10):(5-1):(6-1):(8-1). The magnetic nano-drug according to the present disclosure can position a VEGF ligand through magnetic targeting of hollow zinc ferrite particles, use magnetic particles to regulate reprogramming of macrophages in an intervertebral disc so as to indirectly regulate down-regulation of the VEGF, and inhibit angiogenesis. Meanwhile, the VEGFR is targeted through ligustrazine, controlled release of magnetic heat is combined, and an inhibitory function is achieved. Therefore, double targeting of the magnetic nano-drug can effectively inhibit vascularization, block neurotrophic supply, and implement radical treatment of pain.

DETAILED DESCRIPTION OF THE EMBODIMENTS

In order to better understand the present disclosure, contents of the present disclosure will be further described with embodiments below, which are not limited by the following embodiments. Unless otherwise specified, materials, reagents, etc. used in the embodiments and test examples of the present disclosure may be obtained from commercial sources. Unless otherwise specified, the methods used in the embodiments and the test examples of the present disclosure are all conventional methods.

Embodiment 1

(1) Aminated $ZnFe_2O_4$ hollow porous magnetic nano-particles are prepared as follows: 0.34 g of $ZnCl_2$ (2.5 mmol) and 1.35 g of $FeCl_3 \cdot 6H_2O$ (5 mmol) are dissolved in 40 mL of ethylene glycol, 3.6 g of NaAc and 1.0 g of polyethylene glycol (PEG) 20000 are added, magnetic stirring is conducted for 30 min, and then the mixture is sealed in a 50 mL polytetrafluoroethylene reaction kettle; a high-pressure reaction kettle is heated to 200° C. and kept for 8 h, and is cooled to a room temperature; $PEG-NH_2$ is added, and stirring is conducted for 2 h in a water bath at 50° C.; and a black product obtained is washed with ethanol 3 times and dried for 6 h at 60° C., such that the aminated $ZnFe_2O_4$ hollow porous magnetic nano-particles $ZnFe_2O_4$@PEG-$NH_2$ are obtained.

(2) Silk fibroin modified ligustrazine hydrochloride (LTH-SF) nano-spheres are prepared as follows: 5 mL of silk fibroin (SF) solutions having concentrations of 10 mg/mL and 20 mg/mL are taken separately, 10 mL ligustrazine hydrochloride (LTH) aqueous solutions having concentrations of 0.625 mg/mL and 1.25 mg/mL are added separately, gent stirring is conducted for 20 min, and then 2 mL of anhydrous ethanol is dropped; the mixture is gently stirred for 3 min, and incubation is conducted in a refrigerator at −20° C. for 20 h; after unfreezing at a room temperature, a milky white emulsion is formed; and 5 mL of the prepared emulsion is taken, and dialysis is conducted with 2000 mL of deionized water for 4 h, such that most of LTH that is not wrapped with SF nano-particles or only adsorbed to a surface is removed. Then, the emulsion is freeze-dried, such that the ligustrazine hydrochloride nano-spheres LTH-SF are obtained.

(3) The magnetic nano-drug is prepared as follows: 20 mg of $ZnFe_2O_4$@PEG-$NH_2$ obtained in (1) and 3 mg of LTH-SF obtained in (2) are dissolved in 50 mL of 2-morpholinoethanesulphonic acid (MES) buffer solution (PH=5.0), excessive EDC/NHS (4 mg/2 mg) is added for activation, stirring and mixing reaction is conducted at the room temperature for 48 h, and freeze-drying is conducted after centrifugalization at 2000 rpm, such that the magnetic nano-drug required is obtained.

Figure 1:
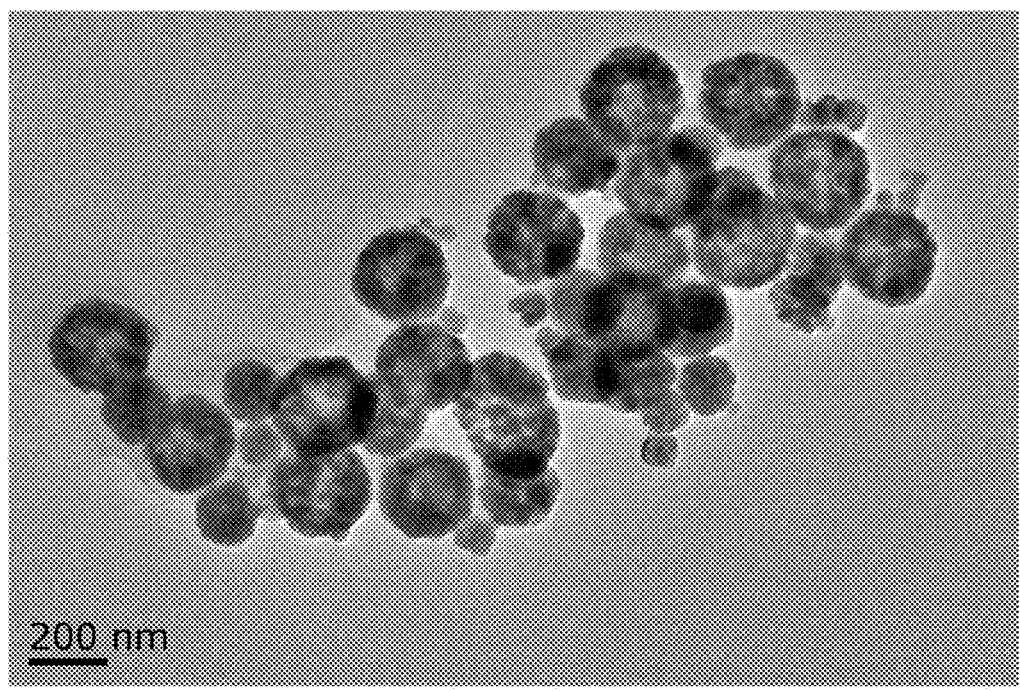
FIG. 1 is a transmission electron microscope (TEM) phenogram of a magnetic nano-drug.

The magnetic nano-drug obtained in Embodiment 1 is scanned with a transmission electron microscope. A scanning result is shown in FIG. 1. As can be seen from FIG. 1, the ligustrazine hydrochloride nano-spheres are well bound to the $ZnFe_2O_4$ hollow porous magnetic nano-particles, such that the magnetic nano-drug having a porous structure can be presented.

Embodiment 2 Influences on Phenotypic
Polarization of Co-Culture of Magnetic
Nano-Particles Having Different Concentrations of
$ZnFe_2O_4$ and Macrophages $ZnFe_2O_4$ magnetic nano-particles prepared in Embodiment 1 are prepared to have concentrations of 10 μg/mL, 50 μg/mL, 100 μg/mL, and 500 μg/mL separately. After autoclaving, the particles are stored at 4° C. for later use. 3 6-well culture plates are prepared and placed for ultraviolet sterilization in a bio-safety cabinet for 1 h. Rat macrophages (NR8383) are prepared into a cell suspension, and inoculated into the sterilized 6-well cell culture plates, with an inoculation density of 1×10$^5$ cells/well, and 2 mL of complete medium (90% DMEM+10% FBS+1% PS) is added. The cell culture plates are transferred to an incubator with 37° C. and 5% $CO_2$, and incubation is conducted for 4 h until cells completely adhere to a wall. The cells are divided into 6 groups, with 3 parallel samples in each group. The six groups are: 20 ng/mL IL-4 (negative control), 100 ng/mL LPS (positive control), 10 μg/mL $ZnFe_2O_4$, 50 μg/mL $ZnFe_2O_4$, 100 μg/mL $ZnFe_2O_4$ and 500 μg/mL $ZnFe_2O_4$. After incubation for 72 h, the culture medium is removed, and the cells are collected and detected with a flow cytometer.

Specific steps of detection with the flow cytometer are as follows: 1) 15 mL of cell staining buffer solution (PBS (PH=7.4)+1% FBS+0.09% $NaN_3$) is added into the cells so as to resuspend, 350×g centrifuging is conducted for 5 min, and supernatant is discarded; 2) coupled fluorescent primary antibodies CD80 (12-0800-82, a mouse source, 1:1000, Thermo Fisher, USA) and incubation is conducted on ice for 15 min-20 min in the dark; 3) washing is conducted twice with 2 mL of cell staining buffer solution, and centrifuging is conducted (350×g, 5 min each time); 4) 0.5 mL of fixed solution is added to fix the cells at the room temperature in the dark for 20 min; 5) 350×g centrifuging is conducted for 5 min, and supernatant is discarded; 6) the fixed cells are resuspended in a cell permeable washing buffer solution, 350×g centrifuging is conducted for 5 min, and washing is conducted twice; 7) coupled fluorescent primary antibodies CD206 (PA5-114370, a rabbit source, 1:1000, Thermo Fisher, USA) are added, and incubation is conducted on ice for 20 min in the dark; 8) 350×g centrifuging is conducted with 2 mL of cell staining buffer solution for 5 min, and washing is conducted twice; and 9) data are collected and analyzed with a flow cytometer.

Figure 2:
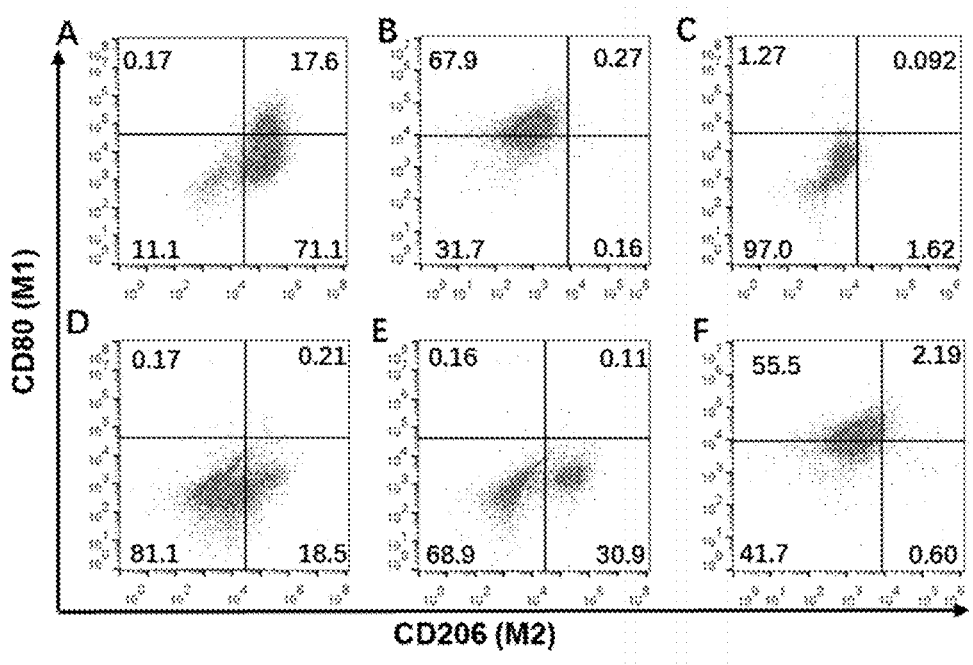
FIG. 2 shows fluorescence activated cell sorting (FACS) detection charts of co-culture of magnetic nano-particles having different concentrations of $ZnFe_2O_4$ and macrophages, where A-E correspond to 20 ng/mL IL-4 (negative control), 100 ng/mL LPS (positive control), 10 μg/mL $ZnFe_2O_4$, 50 μg/mL $ZnFe_2O_4$, 100 μg/mL $ZnFe_2O_4$, and 500 μg/mL $ZnFe_2O_4$, respectively.

Detection results of the flow cytometer are shown in FIG. 2. As can be seen from FIG. 2, $ZnFe_2O_4$ having a lower concentration regulates M2 polarization of macrophages, while $ZnFe_2O_4$ having a higher concentration regulates M1 polarization of macrophages, which may down-regulate expression of VEGF.

Embodiment 3 Influences on VEGF Expressions of
Co-Culture of Magnetic Nano-Particles Having
Different Concentrations of $ZnFe_2O_4$ and
Macrophages $ZnFe_2O_4$ magnetic nano-particles prepared in Embodiment 1 are prepared to have concentrations of 0 μg/mL, 10 μg/mL, 100 μg/mL, and 500 μg/mL separately. After autoclaving, the particles are stored at 4° C. for later use. A 12-well culture plate is placed for ultraviolet sterilization in a bio-safety cabinet for 1 h. Rat macrophages are prepared into a cell suspension, and inoculated into the sterilized culture plate, with an inoculation density of 1×10$^5$ cells/well, and 1 mL of complete medium (90% DMEM+10% FBS+1% PS) is added.

The cell culture plate is transferred to an incubator with 37° C. and 5% $CO_2$, and incubation is conducted for 4 h until cells completely adhere to a wall. The cells are divided into 4 groups, with 3 parallel samples in each group. The four groups are: 0 μg/mL $ZnFe_2O_4$, 10 μg/mL $ZnFe_2O_4$, 100 μg/mL $ZnFe_2O_4$ and 500 μg/mL $ZnFe_2O_4$. After incubation for 24 h, supernatant is collected. The collected supernatant is transferred to a high-speed centrifuge, centrifuging is conducted at 12000 rpm for 5 min, and the supernatant is collected again. The VEGF is quantitatively detected with a rat vascular endothelial growth factor ELISA kit (MM-0179R1, Enzyme Immunosorbent Assay, China), and 3 parallel samples are set for each sample.

Figure 3:
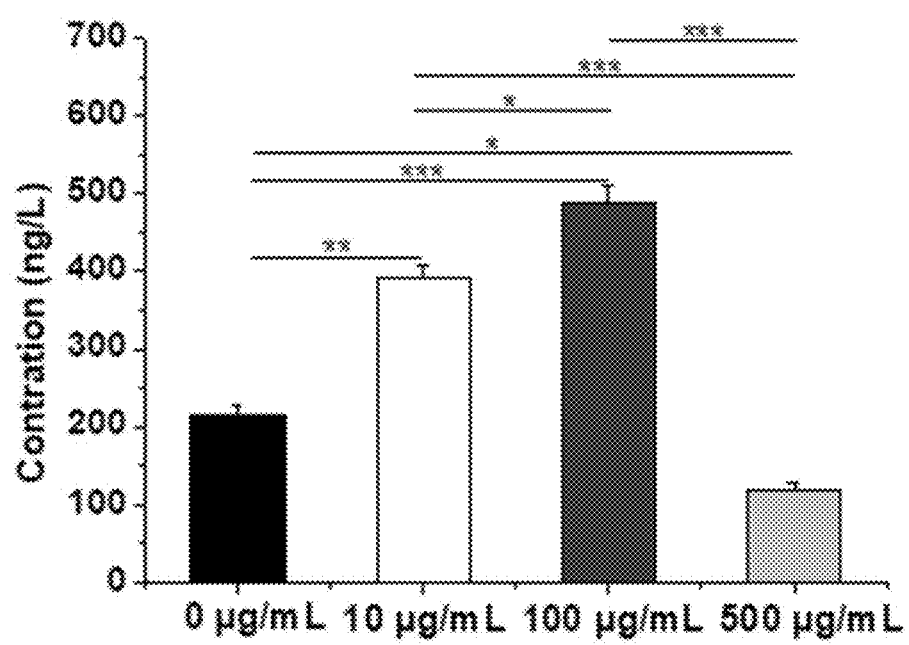
FIG. 3 is an enzyme linked immunosorbent assay (ELISA) result chart of influences on VEGF expressions of co-culture of magnetic nano-particles having different concentrations of $ZnFe_2O_4$ and macrophages.

ELISA detection results are shown in FIG. 3. As can be seen from FIG. 3, $ZnFe_2O_4$ having a lower concentration can promote the VEGF expression, while $ZnFe_2O_4$ having a higher concentration can significantly inhibit the VEGF expression, which show potential of angiogenesis inhibition.

Embodiment 4 Biocompatibility Detection of
Co-Culture of Magnetic Nano-Particles Having
Different Concentrations of $ZnFe_2O_4$ and
Macrophages $ZnFe_2O_4$ magnetic nano-particles prepared in Embodiment 1 are prepared to have concentrations of 0 μg/mL, 10 μg/mL, 100 μg/mL, and 500 μg/mL separately. After autoclaving, the particles are stored at, 4° C. for later use. A 24-well culture plate is placed for ultraviolet sterilization in a bio-safety cabinet for 1 h. Rat macrophages are prepared into a cell suspension, and then inoculated into the culture plate, with an inoculation density of 1×10$^4$ cells/well, and 1 mL of complete medium (90% DMEM+10% FBS+1% PS) is added.

The cell culture plate is transferred to an incubator with 37° C. and 5% $CO_2$, and incubation is conducted for 4 h until cells completely adhere to a wall. The cells are divided into 4 groups, with 3 parallel samples in each group. The four groups are: 0 μg/mL $ZnFe_2O_4$, 10 μg/mL $ZnFe_2O_4$, 100 μg/mL $ZnFe_2O_4$ and 500 μg/mL $ZnFe_2O_4$. The four groups are incubated for 24 h and 48 h respectively, then a culture medium is removed, and non-adherent cells are washed with PBS (0.01 M, PH=7.4) three times.

The mixture of a fresh complete culture medium and a cell-counting-kit (CCK)-8 reagent with a volume ratio of 10:1 is added into the well plate, and transferred to a cell incubator for incubation for 2 h. A suspension is transferred to a 96-well plate (200 L/well), and absorbance is measured at 450 nm with an enzyme-labeled instrument.

Figure 4:
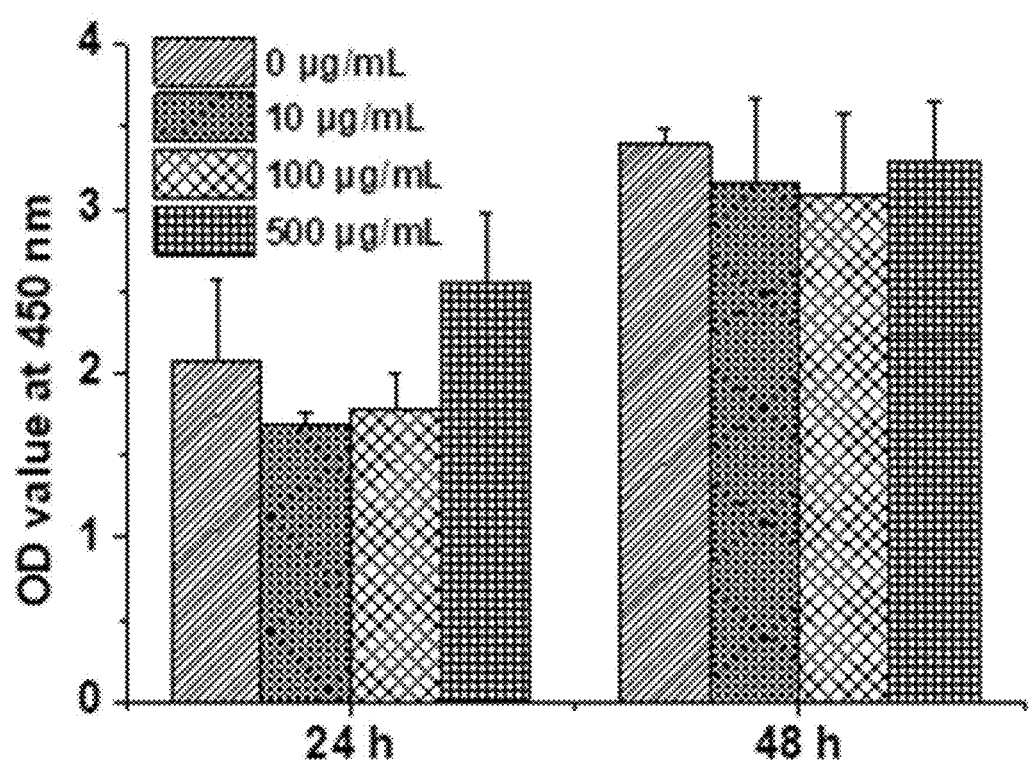
FIG. 4 is a cell-counting-kit (CCK)-8 cell viability assay chart of co-culture of magnetic nano-particles having different concentrations of $ZnFe_2O_4$ and macrophages.

Detection results of a CCK-8 cell viability assay of co-culture of magnetic nano-particles having different concentrations of $ZnFe_2O_4$ and macrophages are as shown in FIG. 4. As can be seen from FIG. 4, 10 μg/mL and 100 μg/mL experimental groups have slightly lower cell viability than a blank control group at 24 h, a difference between which is not significant (P>0.05), and even a 500 μg/mL experimental group has higher cell viability. At 48 h, each experimental group has slightly lower cell viability than the blank control group, without significant difference (P>0.05). It is indicated that the $ZnFe_2O_4$ magnetic nano-particles have high biocompatibility.

Embodiment 5 Influences on Inhibiting VEGF-VEGFR Expressions of Co-Culture of a Magnetic Nano-Drug, Macrophages, and Endothelial Progenitor Cells The magnetic nano-drug prepared in Embodiment 1 is prepared to have a concentration of 400 μg/mL, and is placed in a bio-safety cabinet for ultraviolet sterilization, and then stored at 4° C. for later use. 2 24-well culture plates are placed for ultraviolet sterilization in the bio-safety cabinet for 1 h. Rat macrophages and vascular endothelial cells are prepared into a cell suspension, and inoculated into the culture plates respectively, with an inoculation density of $5\times10^4$ cells/well, and 1.5 mL of complete media (rat macrophage complete medium: 80% F12+20% FBS+1% PS; and vascular endothelial cell complete medium: 90% DMEM+10% FBS+1% PS) are added.

The cell culture plates are transferred to an incubator with 37° C. and 5% $CO_2$, and incubation is conducted for 4 h until cells become stable or adhere to a wall. The cells are divided into 4 groups, with 6 parallel samples in each group. The four groups are: blank control, 400 μg/mL aminated $ZnFe_2O_4$ magnetic nano-particles, 400 μg/mL LTH-SF nano-spheres, and 400 μg/mL magnetic nano-drug. After incubation for 48 h, supernatant is collected with a macrophage culture plate for ELISA detection, and supernatant is removed with an endothelial cell culture plate. The cells are fixed for immunohistochemical staining.

Figure 5:
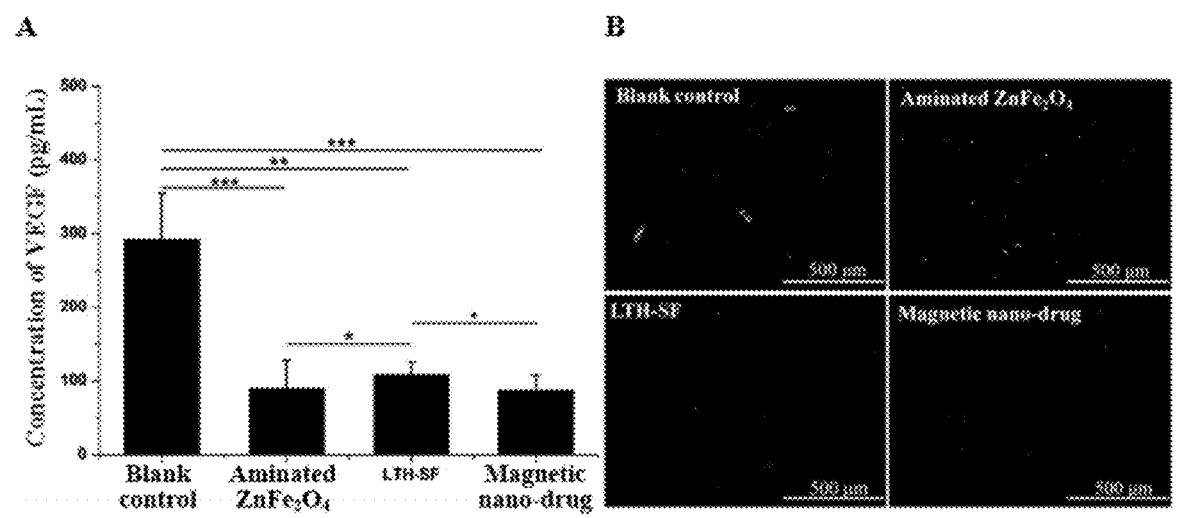
FIG. 5A is an ELISA result chart of influences on VEGF expressions of co-culture of magnetic nano-drugs and macrophages.
FIG. 5B is an immunofluorescence diagram of influences on VEGFR2 expressions of co-culture of magnetic nano-drugs and vascular endothelial cells.

ELISA detection: the collected supernatant is transferred to a high-speed centrifuge, centrifuging is conducted at 12000 rpm for 5 min, and the supernatant is collected again. An ELISA kit is used to detect influences of nano-drugs on secretion of VEGF cytokines by macrophages, where 6 parallel samples are determined for each sample. The ELISA detection results are shown in FIG. 5A. As can be seen from FIG. 5A, the magnetic nano-drug significantly reduces the VEGF expression, which proves potential of down-regulating VEGF to M1 polarization by regulating macrophage reprogramming to inhibit angiogenesis.

Immunofluorescence staining: a 4% paraformaldehyde fixed solution is removed, washing is conducted with PBS 3 times, each time of which lasts 5 min, and primary antibodies VEGFR2 are added dropwise at 4° C. overnight. The primary antibodies are poured out, and washing is conducted with PBS 3 times, each time of which lasts 5 min. A secondary antibody reagent (SA00003-2, Fluorescein (FITC)-conjugated affinipure Goat Anti-Rabbit IgG (H+L), Proteintech, China) is added dropwise, and incubation is conducted at a room temperature for 2 h. PBS washing is conducted for the first time, DAPI counterstaining is conducted for 10 min, and PBS washing is conducted twice, each time of which lasts 5 min. Finally, pictures are observed and collected under a microscope. Immunofluorescence staining results are shown in FIG. 5B. As can be seen from FIG. 5B, both LTH-SF having a concentration of 400 μg/mL and the magnetic nano-drug show significant inhibition of VEGFR2 expression, which show potential of preventing the VEGF ligand from activating a receptor, so as to inhibit vascularized pain transmission and relieve pain.

To sum up, the magnetic nano-drug with double targeting VEGF-VEGFR according to the present disclosure has the potential of inhibiting vascularization in degenerated intervertebral discs and reducing innervation, and has a wide application prospect in treatment of discogenic pain.

What are described above are merely preferred implementations of the present disclosure. It should be noted that those of ordinary skill in the art can also make some improvements and modifications without departing from the principle of the present disclosure, and these improvements and modifications should also fall within the protection scope of the present disclosure.

What is claimed is:

1. A magnetic nano-drug with double targeting vascular endothelial growth factor (VEGF)-vascular endothelial growth factor receptor (VEGFR), comprising aminated zinc ferrite ($ZnFe_2O_4$) hollow porous magnetic nano-particles, ligustrazine hydrochloride nano-spheres lactate dehydrogenase-silk fibroin (LDH-SF), ethylene dichloride (EDC), and n-hydroxy succinimide (NHS), wherein the LDH-SF comprises silk fibroin (SF) and ligustrazine hydrochloride (LTH); and a mass ratio of the aminated $ZnFe_2O_4$ hollow porous magnetic nano-particles to the EDC to the NHS to the LDH-SF is (5-10):(1-5):(1-6):(1-8).

2. The magnetic nano-drug according to claim 1, wherein the aminated $ZnFe_2O_4$ hollow porous magnetic nano-particles are the $ZnFe_2O_4$ hollow porous magnetic nano-particles aminated by polyethylene glycol ($PEG-NH_2$), namely, $ZnFe_2O_4@PEG-NH_2$.

3. The magnetic nano-drug according to claim 1, wherein a mass ratio of the silk fibroin to the ligustrazine hydrochloride is 10:(1-2.5).

4. The magnetic nano-drug according to claim 1, wherein the aminated $ZnFe_2O_4$ hollow porous magnetic nano-particles are chemically combined with the LDH-SF through amide bonds activated by the EDC and the NHS.

5. The magnetic nano-drug according to claim 1, wherein a particle size of the aminated $ZnFe_2O_4$ hollow porous magnetic nano-particles is 20 nanometers (nm)-100 nm.

* * * * *